US006423232B1

(12) United States Patent
Thomas et al.

(10) Patent No.: US 6,423,232 B1
(45) Date of Patent: Jul. 23, 2002

(54) USE OF A NEUTRAL OR CATIONIC POLYMER TO PREVENT ACTIVATION OF THE CONTACT PHASE OF BLOOD OR PLASMA IN CONTACT WITH A SEMI-PERMEABLE MEMBRANE

(75) Inventors: Michel Thomas, Serezin-Du-Rhone; Pierre Valette, Lyon, both of (FR)

(73) Assignee: Hospal Industrie, Meyzieu (FR)

( * ) Notice: Subject to any disclaimer, the term of this patent is extended or adjusted under 35 U.S.C. 154(b) by 0 days.

(21) Appl. No.: 09/657,281

(22) Filed: Sep. 7, 2000

Related U.S. Application Data

(63) Continuation of application No. 09/215,264, filed on Dec. 18, 1998, now Pat. No. 6,177,013.

(30) Foreign Application Priority Data

Dec. 24, 1997 (FR) ............................................. 97/16732

(51) Int. Cl.⁷ ............................................... B01D 61/14
(52) U.S. Cl. ............. 210/650; 210/321.69; 210/321.89; 210/500.24; 210/500.43; 210/645; 264/41; 264/49
(58) Field of Search .......................... 210/321.69, 321.8, 210/321.89, 321.84, 500.23, 506.24, 500.42, 500.43, 636, 645, 646, 650, 651, 500.36, 500.37; 264/41, 48, 49, 417; 428/376, 398; 427/245, 246

(56) References Cited

U.S. PATENT DOCUMENTS

| | | | | |
|---|---|---|---|---|
| 4,545,910 A | * | 10/1985 | Marze | 210/651 |
| 4,749,619 A | | 6/1988 | Angleraud | |
| 4,882,106 A | * | 11/1989 | Johnson et al. | 210/500.24 |

(List continued on next page.)

FOREIGN PATENT DOCUMENTS

| | | |
|---|---|---|
| EP | 0 561 379 | 9/1993 |
| EP | 0 801 953 | 10/1997 |

OTHER PUBLICATIONS

Derwent Publications Ltd., London, GB, XP002079254 Nov. 10, 1995.
EP 0801953—English Abstract.

Primary Examiner—Joseph W. Drodge
(74) Attorney, Agent, or Firm—Millen, White, Zelano & Branigan, P.C.

(57) ABSTRACT

A method for preventing activation of the contact phase of blood or plasma which comes into contact with a semi-permeable membrane based on polyacrylonitrile bearing fixed negative charges, which is fitted in apparatus for the treatment of blood or plasma, by extra-corporal circulation, said method comprising contacting blood or plasma with said semi-permeable membrane, wherein: a neutral or cationic polymer is combined with said semi-permeable membrane before or after formation of the membrane, and before sterilization of the membrane; the overall ionic capacity of the semi-permeable membrane, based on polyacrylonitrile bearing fixed negative charges and containing a neutral or cationic polymer, is negative; the overall ionic capacity of the semi-permeable membrane, based on polyacrylonitrile bearing fixed negative charges and containing a neutral or cationic polymer, is, as an absolute value, not more than 10% less than the overall ionic capacity of the same semi-permeable membrane without a neutral or cationic polymer, at least one of said polymer being present at the surface of the membrane; the semi-permeable membrane based on polyacrylonitrile bearing fixed negative charges and containing a neutral or cationic polymer complies, before sterilization, with the following two electrical characteristic: the electrokinetic index "I" is less than or equal to 0.8, "I" being equal to the logarithm, in base 10, of the ratio $|Z|/R$, where "Z" is the Zeta potential, as an absolute value, expressed in microvolts, of the surface of the membrane intended to come into contact with blood or plasma, and where "R" is the electrical resistivity of the membrane, expressed in ohm.centimeters, and the Zeta potential "Z" is negative.

22 Claims, 1 Drawing Sheet

U.S. PATENT DOCUMENTS

| | | |
|---|---|---|
| 5,039,420 A | 8/1991 | Klein et al. |
| 5,145,583 A | 9/1992 | Angleraud et al. |
| 5,236,592 A | 8/1993 | Dejardin et al. |
| 5,840,190 A | 11/1998 | Scholander et al. |
| 5,919,370 A | 7/1999 | Rottger et al. |
| 6,177,013 B1 * | 1/2001 | Thomas et al. ........ 210/500.43 |

* cited by examiner

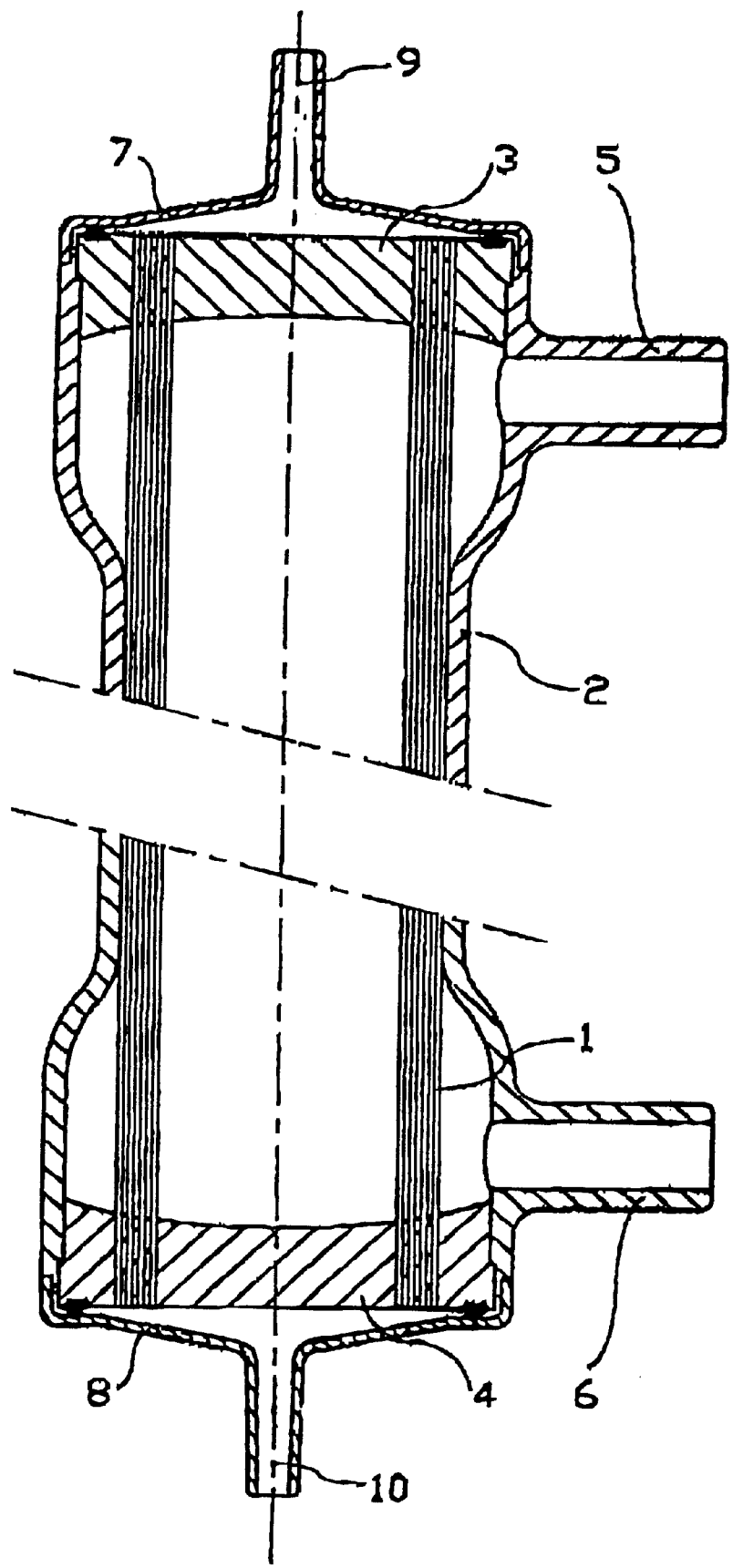

USE OF A NEUTRAL OR CATIONIC POLYMER TO PREVENT ACTIVATION OF THE CONTACT PHASE OF BLOOD OR PLASMA IN CONTACT WITH A SEMI-PERMEABLE MEMBRANE

This application is a continuation of application Ser. No. 09/215,264 filed Dec. 18, 1998, now U.S. Pat. No. 6,177,013 claiming priority of French application 97/16732 filed Dec. 24, 1997.

The present invention relates to the use of a neutral or cationic polymer, combined, before sterilization, with a semi-permeable membrane based on polyacrylonitrile bearing fixed negative charges, which is fitted in apparatus for the treatment of blood or plasma by extra-corporal circulation, to prevent activation of the contact phase of blood or plasma.

The subject of the present invention is also apparatus for the treatment of blood or plasma by extra-corporal circulation, which prevents activation of the contact phase of blood or plasma, as well as processes for manufacturing this apparatus.

Apparatus for the treatment of blood or plasma by extra-corporal circulation is used in various medical or paramedical applications, such as: treatment of renal insufficiency by dialysis or haemofiltration, plasmapheresis and apheresis for therapeutic and non-therapeutic purposes, oxygenation of the blood, immunopurification, etc.

Activation of the contact phase of blood or plasma appears to take place in particular when apparatus for the treatment of blood or plasma by extra-corporal circulation is used, which includes a negatively-charged semi-permeable membrane, without, in the absence of disruptive factors, the patients experiencing the slightest discomfort. Activation of the contact phase is described as a biological phenomenon which takes place in the case of patients undergoing blood (or plasma) treatment by extra-corporal circulation, when the blood comes into contact with the negatively charged surface of the membrane of certain apparatus for blood and plasma treatment. This biological phenomenon results in the generation of active substances, kallicrein and factor XIIa from inactive substances, prekallicrein and factor XII, kallicrein having a catalytic effect on the production of factor XIIa, and vice versa. In addition, kallicrein is the cause of the transformation of a plasma protein, high molecular weight kininogen, into a peptide substance, bradykinin.

When activation of the contact phase takes place simultaneously with certain disruptive factors such as, for example:

the presence, in the blood to be treated, of medicinal products for combating arterial hyper-tension by inhibition of the natural mechanism of vasoconstriction, these products being referred to generically as conversion enzyme inhibitors, or CEIs. These CEIs are also used for other therapeutic applications, in particular for treating certain forms of cardiac insufficiency, dilution of the blood entering the apparatus filled with saline solution and concomitant lowering of the blood pH, activation of the contact phase appears to be the cause of adverse reactions called anaphylactoid.

These anaphylactoid reactions develop, a few minutes after the start of the treatment, by various symptoms, including a generalized sensation of hotness, swelling of the fingers, the lips or the tongue, gasping for breath, nausea and laryngeal oedema.

Anaphylactoid reactions have been observed in particular in the case of renal insufficiency patients treated by haemodialysis, haemofiltration or haemodiafiltration with the aid of apparatus for the treatment of the blood in the form of a dialyser or exchanger containing a membrane.

Anaphylactoid reactions have been observed with exchangers containing membranes of various chemical compositions, sometimes during a first use, sometimes after several uses when the exchangers, rather than being discarded after a single use, are reused several times and recycled after each use. As examples of exchangers for which a first use has been accompanied by an adverse reaction, mention may be made of dialysers containing a membrane based on polymethyl methacrylate and on polyacrylonitrile. Reactions associated with the reuse of dialysers containing a membrane based on cellulose acetate and on polysulphone have also been well documented (see the article entitled "Anaphylactoid reactions associated with reuse of hollow-fibber haemo-dialysers and ACE inhibitors" in "Kidney International", vol. 42 (1992), pp. 1232–1237).

Anaphylactoid reactions are ascribed to an excessive concentration of bradykinin in the blood or in the plasma.

In order to avoid the generation of bradykinin at a concentration above 4000 pg/ml, European patent No. 0,561,379 recommends placing the blood or the plasma in contact only with semi-permeable membranes which have a limited surface charge density, i.e. an overall surface electrical charge of greater than or equal to $-30$ $\mu$eg/g of membrane, this electrical charge being measured by a method chosen from the group consisting of the dye adsorption method, the salt cleavage method, the method of titration to neutralization and the iodine method.

However, from the description of the invention claimed in European patent No. 0,561,379, in particular from the measuring methods proposed, it emerges that the surface electrical charge in fact corresponds to the overall ionic capacity of the semi-permeable membranes. Consequently, this European patent relates only to semi-permeable membranes with an overall ionic capacity of greater than or equal to $-30$ $\mu$eq/g of membrane, but not to semi-permeable membranes with an overall ionic capacity of very much less than $-30$ $\mu$eq/g of membrane, such as, for example, the membrane manufactured by the company Hospal from a copolymer of acrylonitrile and of sodium methallyl sulphonate, which is known under the trade name AN69.

Now, it is desirable not to modify the ionic capacity of membranes since this capacity gives rise to the adsorption and/or transfer of: certain proteins such as $\beta$2-microglobulin, inflammation mediators and complement factors; lipids. This is particularly true for membranes with a homogeneous, symmetrical structure.

Moreover, the Applicant has observed, that on several examples, that a membrane which has an overall ionic capacity of greater than $-30$ $\mu$eq/g of membrane can lead to activation of the contact phase, whereas, conversely, a membrane with an overall ionic capacity which is markedly less than $-30$ $\mu$eq/g of membrane cannot lead to activation of the contact phase.

Given the preceding observations, at the present time, a solution which is satisfactory, in both medical and economic terms, for preventing activation of the contact phase of blood or plasma which comes into contact with a negatively-charged semi-permeable membrane does not appear to be known.

SUMMARY OF THE INVENTION

One aim of the invention is thus to solve the abovementioned problem with apparatus for the treatment of blood or plasma by extra-corporal circulation, comprising a semipermeable membrane based on polyacrylonitrile bearing fixed negative charges, which possesses two characteristics that have hitherto been considered antinomic, i.e.:
  a negative overall ionic capacity, corresponding to an excess of negative charges, which simultaneously participates in the biocompatibility of the membrane and is a factor for triggering activation of the contact phase, and
  a capacity not to produce activation of the contact phase under normal conditions for a first use.

Another aim of the invention is to solve the above-mentioned problem with sterilized apparatus for the treatment of blood or plasma by extra-corporal circulation, which has a capacity not to produce activation of the contact phase under normal conditions for a first use and which is stable in storage. Lastly, another aim of the invention is sterilized apparatus for the treatment of blood or plasma by extra-corporal circulation, which has a capacity not to produce activation of the contact phase under normal conditions for a first use and which is ready to use, i.e. which does not require any special manipulation on the part of the user of the apparatus, such as a special manipulation for the purposes of preventing the adverse effects of activation of the contact phase.

To this effect, the invention proposes the use of a neutral or cationic polymer for preventing activation of the contact phase of blood or plasma which comes into contact with a semi-permeable membrane based on poly-acrylonitrile bearing fixed negative charges, which is fitted in apparatus for the treatment of blood or plasma, by extra-corporal circulation, according to which:

(1) the neutral or cationic polymer is combined with this semi-permeable membrane, before or after formation of the membrane, and before sterilization of the membrane;

(2) the overall ionic capacity of the semi-permeable membrane, based on polyacrylonitrile bearing fixed negative charges and containing a neutral or cationic polymer, is negative;

(3) the overall ionic capacity of the semi-permeable membrane, based on polyacrylonitrile bearing fixed negative charges and containing a neutral or cationic polymer, is, as an absolute value, not more than 10% less than the overall ionic capacity of the same semi-permeable membrane which does not contain a neutral or cationic polymer; preferably, it is, as an absolute value, not more than 1% less than the overall ionic capacity of the same semi-permeable membrane which does not contain a neutral or cationic polymer;

(4) the semi-permeable membrane containing a neutral or cationic polymer complies, before sterilization, with one or other of the following two electrical characteristics:
  the electrokinetic index "I" which is equal to $Log_{10}$ (|Z|/R), i.e. to the logarithm, in base 10, of the ratio |Z|/R of the Zeta potential "Z", as an absolute value, expressed in microvolts (or $\mu V$), of the surface of the membrane intended to come into contact with the blood or plasma, to the electrical resistivity "R" of the membrane, expressed in ohm.centimetres (or $\Omega \cdot cm$), is less than or equal to 0.8, or
  the Zeta potential "Z" is positive and is between 0 and +15 mV (limits not included).

Preferably, the electrokinetic index "I" is less than or equal to 0.7 and better still less than or equal to 0.6.

Preferably, when the Zeta potential is positive, it is strictly less than 15 mV and greater than or equal to 1 mV. Better still, the Zeta potential is greater than or equal to 6 mV and strictly less than 15 mV.

In order to obtain the electrokinetic index "I":
  the Zeta potential "Z" is calculated by measuring the potential "E", expressed in volts, created by the flow of an electrolyte ($10^{-2}$M NaCl), for example inside a bundle of hollow fibers. This potential "E", measured between two Ag/AgCl electrodes connected to a high-impedance volt-meter (Keithley 617), is linked to the Zeta potential "Z", expressed in volts, by the Helmholtz-Smoluchowski law:

$$Z = \frac{4\pi v \lambda E}{\varepsilon P}$$

where:
  P is the hydrostatic pressure giving rise to the flow of the electrolyte, in millimetres of mercury (mmHg) (the ratio E/p is referred to as the flow potential),
  v is the dynamic viscosity of the electrolyte, in Pascals,
  $\lambda$ is the actual electrical conductivity of the system in equilibrium with the electrolyte (obtained by measuring the resistance with $10^{-2}$M NaCl) and is expressed in Siemens/m,
  $\in$ is the dielectric constant of the electrolyte, or the permittivity.
  and the electrical resistivity "R", expressed in $\Omega \cdot cm$, is deduced by measuring the electrical resistance of the semi-permeable membrane in equilibrium with an electrolyte ($5 \times 10^{-5}$M NaCl), using a Wheatstone bridge which functions with an alternating current (Wawetek generator, model 19, frequency 10 Hz).

The experimental determination of the electrical characteristics of the semi-permeable membrane containing a neutral or cationic polymer must be carried out before sterilizing the membrane in the case of a sterilization by irradiation. Otherwise, the obtained values are nonsensical and can not be directly in correlation with the amount of neutral or cationic polymer to be used. In the other, less energetic modes of sterilization, such as sterilization with ethylene oxide, this experimental determination can be carried out before or after sterilization.

In the context of the invention, it is estimated that activation of the contact phase is effective as soon as the maximum concentration of kallicreins (KK) produced during the first 10 minutes of contact with blood or plasma exceeds 10 units of kallicreins (KK) per litre of blood or plasma (10 UKK/l), taking into account the sensitivity of the chromogenic test used.

The term "semi-permeable membrane" is intended to refer to a flat membrane or a bundle of hollow fibers. Consequently, the apparatus for the treatment of blood or plasma by extra-corporal circulation generally comprises two compartments separated by the semi-permeable membrane.

The expression "semi-permeable membrane based on polyacrylonitrile bearing fixed negative charges" is intended to refer to a semi-permeable membrane consisting of poly-acrylonitrile to which anionic functional groups are attached via covalent bonds, this negatively-charged polyacrylonitrile not being water-soluble.

The expression "neutral or cationic polymer combined (or incorporated) with the semi-permeable membrane" is intended to mean that this polymer is introduced:
  either into the mass of the negatively-charged polyacrylonitrile (this process is more particularly suitable for the neutral polymer), or to the surface of the semi-permeable membrane, for example by placing the membrane in contact with a solution containing the polymer (this process is more particularly suitable for the cationic polymer) or by spraying with a solution containing the polymer.

In addition, the operating conditions for carrying out this combination (or incorporation) are designed to promote the presence of at least some of the neutral or cationic polymer at the surface of the semi-permeable membrane (for example by promoted migration of the neutral polymer or ionic bonding of the cationic polymer).

The term "swollen polymer" is intended to refer here to the membrane hydrated to the content corresponding to the clinical use.

Surprisingly, it has been found that it is possible to prevent activation of the contact phase, which can occur fleetingly during the use of apparatus for the treatment of blood or plasma by extra-corporal circulation, by means of a semi-permeable membrane based on polyacrylonitrile bearing fixed negative charges, by modifying the electrical characteristics of the membrane, so that one or other of the following two conditions are satisfied, before sterilization:

the electrokinetic index "I", which is equal to $Log_{10} |Z|/R$, is less than or equal to 0.8, or the Zeta potential "Z" is positive and ranges between 0 and +15 mV (limits not included), while at the same time substantially maintaining the overall ionic capacity of the membrane, the modification of these electrical characteristics being obtained by combining this membrane with a suitable amount of neutral or cationic polymer, this combination being carried out:

firstly, before sterilization, secondly, before or after formation of this membrane.

The prevention of activation of the contact phase has in particular been obtained with semi-permeable membranes based on highly negatively-charged polyacrylonitrile, reaching overall ionic capacities of less than or equal to $-100$ μeq/g of swollen polymer.

Surprisingly also, sterilization of the apparatus has no influence on its capacity to prevent activation of the contact phase.

Under the normal conditions of use of the apparatus according to the invention, the known qualities of the semi-permeable membrane are kept intact when this same membrane contains a neutral or cationic polymer: for example, for a haemodialysis/haemofiltration membrane, the haemocompatibility, the performance levels in terms of diffusive and convective transfers, the capacity for adsorbing undesirable substances, etc, are kept intact.

In addition, interestingly, it has not been noticed adsorption of the anticoagulant agents, such as heparin, in a semi-permeable membrane, based on polyacrylonitrile bearing fixed negative charge, modified according to the present invention, in the case the sterilization is carried out by irradiation.

According to the invention, the semi-permeable membrane based on negatively-charged polyacrylonitrile, before combination with a neutral or cationic polymer, has a density of electronegative surface charges corresponding to excesses of negative charges which can be detected, in particular by the electrokinetic potential measurements (Zeta potential). The neutral or cationic polymer makes it possible to mask, at least partly, the electronegative charges present at the surface of the membrane. In the case of a cationic polymer, the negative charges on the membrane are masked in particular by ionic bonding.

Preferably, the neutral polymer is water-soluble at room temperature (about 20° C.).

Preferably, the cationic polymer is water-soluble at room temperature (about 20° C). However, a cationic polymer which is soluble in an organic solvent, such as alcohols, may be suitable for the invention.

The neutral or cationic polymer must be able to withstand energetic sterilization, such as gamma irradiation. In other words, at least some of the polymer must remain intact and be able to mask, in the desired manner, some of the electronegative surface charges of the membrane. Moreover, the polymer fixed to the membrane and irradiated must not become toxic.

The weight-average molecular mass of the polymer is at least equal to 10,000 daltons.

Advantageously, the weight-average molecular mass of the neutral polymer is greater than 40,000 daltons, preferably greater than 100,000 daltons, and the average molecular mass of the cationic polymer is greater than 25,000 daltons, preferably greater than 100,000 daltons. These molecular masses are measured by a light-scattering method. As polymers which are suitable for carrying out the present invention, mention may be made, as neutral polymers, of polyvinylpyrrolidones (PVP) and polyethylene glycols (PEG) of different molecular masses; as cationic polymers, mention may be made of hydrophilic cationic polymers capable of being adsorbed onto a semi-permeable membrane which has an electronegative surface charge density, such as polyamines, for example polyethyleneimines (PEI), diethylaminoethyl dextrans or DEAE dextrans, and polymers and copolymers containing one or several quaternary ammonium groups.

According to a preferred embodiment of the invention, the polymer is cationic. Preferably also, it is chosen from polyethyleneimines (PEI).

The amount of neutral or cationic polymer to be combined with the membrane depends on the electrical characteristics (Z, R, I) targeted and is variable depending on the chemical nature of the polymer, but does not exceed 10% of the mass of polyacrylonitrile. This amount is generally not more than 2% of the mass of polyacrylonitrile constituting the membrane in the case of the neutral polymer.

The amount of cationic polymer to be combined with the membrane is preferably between about 1 and about 10 mg per m² of membrane intended to be in contact with blood or plasma (this amount is very much less than 1% of the mass of polyacrylonitrile constituting the membrane).

The invention is particularly suitable for semi-permeable membranes based on polyacrylonitrile bearing fixed negative charges which give it a high absolute value of overall ionic capacity, even after incorporation of the neutral or cationic polymer.

Thus, the invention is particularly suitable for semi-permeable membranes, based on polyacrylonitrile bearing fixed negative charges and containing a neutral or cationic polymer, which have an overall ionic capacity of less than $-30$ μeq per g of swollen polymer (i.e. the membrane), preferably less than $-50$ μeq per g of swollen polymer, as measured by the standard ion-exchange method: by way of reference, the electronegative polymer used to prepare the membrane made of AN69 has an overall ionic capacity or density of negative charges equal to about $-180$ μeq per g of swollen polymer.

Advantageously, the semi-permeable membrane is a flat membrane or a bundle of hollow fibers based on an acrylonitrile homopolymer or copolymer and combined with a neutral or cationic polymer. As examples of acrylonitrile copolymers, mention may be made of:

(1) a copolymer of acrylonitrile and of at least one anionic or anionizable monomer containing, where appropriate, units derived from at least one other monomer containing olefinic unsaturation which is capable of being copolymerized with acrylonitrile, or (2) a copolymer of acrylonitrile and of at least one nonionic and non-ionizable monomer containing, where appropriate, units derived from at least one other monomer containing olefinic unsaturation which is capable of being copolymerized with acrylonitrile.

Some of these polyacrylonitriles, as well as the various monomers which can be selected as starting materials, and their manufacture, are described more fully in U.S. Pat. No. 4,545,910 reissued under No. Re.34239.

Among these polyacrylonitriles, those with which the invention is particularly suitable are defined under (1) above. In particular, the invention is particularly suitable for those for which the anionic or anionizable comonomer is olefinically unsaturated and bears anionic groups chosen from sulphonate, carboxyl, phosphate, phosphonate and sulphate groups, and, even more particularly, when this comonomer is sodium methallyl sulphonate.

The precise nature of the counterion for the anionic groups is not essential for the correct functioning of the invention.

A subject of the invention is also processes for manufacturing apparatus for the treatment of blood or plasma by extra-corporal circulation, for preventing activation of the contact phase and comprising a semi-permeable membrane in the form of a flat membrane or a bundle of hollow fibers, based on polyacrylonitrile bearing fixed negative charges and combined with a neutral or cationic polymer.

A first manufacturing process comprises the steps of: preparing a solution consisting of:

at least one polyacrylonitrile bearing fixed negative charges, at least one neutral polymer, in an amount adjusted in order to obtain the four characteristics (1)–(4) abovementioned, at least one solvent for the said polyacrylonitrile and for the neutral polymer, optionally, at least one non-solvent for the polyacrylonitrile; extruding this solution in order to form a hollow fiber or a flat membrane;

simultaneously, in the case of the preparation of a hollow fiber, or after extrusion in the case of the formation of a flat membrane, solidifying the membrane obtained by a phase inversion process by partial or total contact of the extruded product with a liquid or gaseous fluid which is chemically inert with respect to the said polymers;

washing the flat membrane or the hollow fiber obtained;

optionally, treating the flat membrane or the hollow fiber with glycerol;

preparing a semi-permeable membrane from the flat membrane or assembling a bundle of hollow fibers from the hollow fiber;

mounting the flat membrane or the bundle of hollow fibers in a case and, where appropriate, fixing caps to the case;

sterilizing the medical apparatus obtained.

When the polymer is cationic, it can be combined with the semi-permeable membrane after the extrusion step for obtaining a hollow fiber or a flat membrane, according to a second process comprising the steps of:

(a) preparing a flat membrane or a hollow fiber, which has optionally been treated with glycerol, by a conventional process from a solution of polyacrylonitrile bearing negative charges;

(b) assembling, in a conventional manner, the various components of the apparatus, in particular mounting the semi-permeable membrane or a bundle of hollow fibers in a case and attaching the caps to this case;

(c) simultaneously or successively, optionally removing the glycerol from the semi-permeable membrane and preparing a solution containing the cationic polymer in dissolved form and bringing this solution into contact with the surface of the semi-permeable membrane intended to be placed in contact with blood, it being possible for step (c) to be carried out before or after step (b), the amount of cationic polymer being adjusted in order to obtain the four characteristics (1)–(4) abovementioned, (d) when the abovementioned step (c) has been carried out subsequent to step (b), purging the apparatus of the solution containing the cationic polymer;

(e) optionally, rinsing the semi-permeable membrane in order to remove the excess of non-bound cationic polymer and, optionally, retreating the semi-permeable membrane with glycerol;

(f) sterilizing the medical apparatus.

Advantageously, the cationic polymer is water-soluble and the solution in which this polymer is dissolved is aqueous.

In the case of a flat semi-permeable membrane, this membrane can be combined with a neutral or cationic polymer, preferably a cationic polymer, using a spraying process comprising the following steps:

(a) preparing a flat membrane, which has optionally been treated with glycerol, from a solution of polyacrylonitrile bearing negative charges;

(b) simultaneously or consecutively, optionally removing the glycerol from the semi-permeable membrane and preparing a solution containing the cationic or neutral polymer in dissolved form and spraying this solution onto the surface of the semi-permeable membrane intended to be placed in contact with blood, the amount of cationic or neutral polymer being adjusted in order to obtain the four characteristics (1)–(4) abovementioned,;

(c) assembling the various components of the apparatus, in particular mounting the semi-permeable membrane in a case and attaching the caps to this case;

(d) optionally, rinsing the semi-permeable membrane in order to remove the excess of non-bound cationic polymer and, optionally, retreating the semi-permeable membrane with glycerol;

(f) sterilizing the medical apparatus.

In addition, in the context of the above-mentioned processes for manufacturing apparatus for the treatment of blood or plasma by extra-corporal circulation, for preventing activation of the contact phase and comprising a semi-permeable membrane in the form of a flat membrane or a bundle of hollow fibers, based on polyacrylonitrile bearing fixed negative charges and combined with a neutral or cationic polymer, the amount of polymer, whether it is neutral or cationic, is adjusted so as to satisfy the following conditions:

the overall ionic capacity of the semi-permeable membrane, based on polyacrylonitrile bearing fixed negative charges and containing a polymer (neutral or cationic), is negative;

the overall ionic capacity of the semi-permeable membrane, based on polyacrylonitrile bearing fixed negative charges and containing a polymer (neutral or cationic), is, as an absolute value, not more than 10% less than the overall ionic capacity of the same semi-permeable membrane which does not contain polymer (neutral or cationic); preferably, it is, as an absolute value, not more than 1% less than the overall ionic capacity of the same semi-permeable membrane which contains no polymer;

the electrical characteristics of the semi-permeable membrane containing a polymer (neutral or cationic) satisfies one or other of the following two conditions:

the electrokinetic index "I" is equal to $Log_{10}(|Z|/R)$, i.e. to the logarithm, in base 10, of the ratio $|Z|/R$ of the Zeta potential "Z", as an absolute value, expressed in microvolts (or $\mu V$), of the surface of the membrane intended to come into contact with the blood or plasma, to the electrical resistivity "R" of the membrane, expressed in ohm.centimetres (or $\Omega \cdot cm$), is less than or equal to 0.8, or the Zeta potential "Z" is positive and is between 0 and +15 mV (limits not included).

Preferably, the electrokinetic index "I" is less than or equal to 0.7 and better still less than or equal to 0.6.

Preferably, when the Zeta potential is positive, it is greater than or equal to 1 mV and strictly less than 15 mV.

Other operating conditions for preparing the semi-permeable membrane may be found in U.S. Pat. No. 4,749,619 (gelation process) or in U.S. Pat. No. 4,056,467 (coagulation process).

Depending on the case, the sterilization technique which will be used, without any significant effect on the bonding between the neutral or cationic polymer and the semi-permeable membrane based on polyacrylonitrile, may be sterilization by irradiation, in particular by gamma irradiation, or sterilization with ethylene oxide.

The abovementioned processes for manufacturing apparatus for the treatment of blood or plasma by extra-corporal circulation have a major advantage: the apparatus obtained does not require any specific manipulation on the part of the user, in particular during the phases of rinsing and priming the apparatus, and the use of the apparatus by the user is entirely identical to that of any apparatus of the same type.

Lastly, the invention relates to apparatus for the treatment of blood or plasma by extra-corporal circulation, which is sterilized and ready to use, for preventing activation of the contact phase and comprising a semi-permeable membrane, in the form of a flat membrane or a bundle of hollow fibers, based on polyacrylonitrile bearing fixed negative charges, characterized in that, before or after formation of the semi-permeable membrane, and before sterilization, at least one neutral or cationic polymer is incorporated into the semi-permeable membrane, in a suitable amount such that:

the overall ionic capacity of the semi-permeable membrane, based on polyacrylonitrile bearing fixed negative charges and containing a neutral or cationic polymer, is negative;

the overall ionic capacity of the semi-permeable membrane, based on polyacrylonitrile bearing fixed negative charges and containing a neutral or cationic polymer, is, as an absolute value, not more than 10% less than the overall ionic capacity of the same semi-permeable membrane which contains no neutral or cationic polymer;

the semi-permeable membrane based on polyacrylonitrile bearing fixed negative charges and containing a neutral or cationic polymer complies with one or other of the following electrical characteristics:

the electrokinetic index "I" of the membrane containing a neutral or cationic polymer is less than or equal to 0.8, "I" being equal to the logarithm, in base 10, of the ratio $|Z|/R$, where "Z" is the Zeta potential, as an absolute value, expressed in microvolts, of the surface of the membrane intended to come into contact with blood or plasma, and where "R" is the electrical resistivity of the membrane, expressed in ohm.centimetres, or the Zeta potential is positive and ranges between 0 and +15 mV (limits not included).

Preferably, the electrokinetic index "I" is less than or equal to 0.7 and better still less than or equal to 0.6.

Preferably, when the Zeta potential is positive, it is greater than or equal to 1 mV and strictly less than 15 mV.

NON-LIMITING ILLUSTRATIVE EXAMPLES OF THE INVENTION

Example 1

A minidialyser comprising 170 hollow fibers made of AN69 (membrane consisting of a copolymer of acrylonitrile and of sodium methallyl sulphonate) was assembled. The blood compartment, or internal compartment, is delimited by the interior of the fibers and two caps, each fitted with an access tube, fixed to the ends of the case of the minidialyser.

Each fiber has the following dimensions:

inside diameter: 240 $\mu m$, wall thickness: 50 $\mu m$, length: 18 cm.

The inner surface area intended to come into contact with the blood or plasma is about 230 $cm^2$.

A solution of polyethyleneimine (PEI P, BASF, with an average molecular mass of 750,000 daltons) is prepared in a water/sodium chloride mixture (0.15 M NaCl).

The PEI concentration is 40 mg/l.

8 ml of this solution is circulated in the internal compartment of the minidialyser at a flow rate of 4 ml/min. 20 ml of aqueous 0.15 M NaCl solution for rinsing is then circulated in this same compartment at a flow rate of 4 ml/min.

Under these conditions, the amount of PEI bound to the membrane is about 4 $mg/m^2$ (determined by measuring out the PEI leaving the minidialyser).

The fibers thus treated are then retreated with glycerol by circulation of a glycerol/water mixture (60/40 by mass), in a proportion of 20 ml with a flow rate of 4 ml/min, and purged with air in order to remove the excess of mixture.

This minidialyser is sterilized with ethylene oxide.

Comment Regarding the Change in the Ionic Capacity

The initial overall ionic capacity of the AN69 membrane is about −200 $\mu eq/g$ of swollen polymer.

If we consider the general formula of PEI —$(CH_2$—$CH_2$—$NH)_n$—, this contains about 23 $\mu mol$ of amine groups per mg of PEI.

In the hypothesis in which all the amine groups are tonically linked to the sulphonate groups of AN69 (which is not physically possible), a simple calculation shows that the reduction in the overall ionic capacity of the membrane is negligible (about 0.8%).

Capacity of this Minidialyser to Prevent the Activation of the Contact Phase

Prior to this test, the minidialyser is rinsed by circulating 20 ml of a 0.15M NaCl solution at a flow rate of 2 ml/min.

A biological liquid, capable of stimulating the production of kallicreins on contact with a negatively-charged surface membrane, was prepared. The biological liquid used for the test consisted of platelet-poor human plasma, diluted to 5% in physiological saline supplemented with citrate as anticoagulant (it is noted that the conditions of the test used are different from the conditions for using apparatus for extracorporal circulation of blood: the dilution rate is very high, the liquid chosen is plasma and not blood, the plasma is supplemented with citrate, and thus acidified, whereas, in dialysis, the anticoagulant used is heparin. These test conditions are chosen intentionally since they stimulate and amplify the activation of the contact phase). This liquid is circulated in an open circuit in the internal compartment of the minidialyser at a flow rate of 2 ml/min for 3 minutes. The plasmatic kallicreins were measured out in samples of liquid taken after an interval of time by means of a standard chromogenic test, using the substrate S2302 from the company Biogenic.

As shown in Table 1, this treatment substantially modifies the electrical characteristics of the membrane and has the effect of inhibiting the activation of the contact phase.

TABLE 1

Electrical characteristics and level of activation of the contact phase of the membranes AN69 and AN69 modified with PEI.

| Membrane | Zeta potential mV | Resistivity ohm.cm | Electro-kinetic index I | Concentration of kallicreins formed, in U/l |
|---|---|---|---|---|
| AN69 | −70 | 312 | 1.98 | 70 |
| AN69 modified with PEI | −1 | 312 | 0.5 | <10 |

Example 2

The solutions (2a and 2b) below are obtained using an extruder screw at a temperature of about 130° C. Table 2A gives the compositions of these solutions, expressed as a percentage by mass.

TABLE 2A

| Solution | Dralon L a) | DMF b) | 2-Butoxyethanol | PVP c) |
|---|---|---|---|---|
| 2a | 28% | 51 | 21% | 0 |
| 2b | 28% | 50.5% | 21% | 0.5% | a) copolymer of acrylonitrile and of vinyl acetate, sold under the name Dralon L by Bayer
b) dimethylformamide
c) polyvinylpyrrolidone K90 sold by the company Aldrich, with an average molecular mass equal to 360,000 daltons.

These solutions are extruded through a tubular die whose dimensions are 1200/860/520 µm. The internal fluid is nitrogen. After cooling with ambient air (20° C.), the heat-reversible gel obtained is washed with water and diluted by a factor of 2 in the water at 60° C. The membrane obtained is treated with glycerol by immersing in a glycerol/water mixture (60/40 by mass).

The overall ionic capacity of the membrane obtained from the solution (2a) is about −20 µeq/g of swollen polymer and that of the membrane obtained from the solution (2b) is equal to about −19 µeq/g.

Minidialysers (identical to those described in Example 1) are made with these membranes.

The minidialysers are sterilized by gamma irradiation (25/36 kGy).

The rinsing operation and the biological test (activation of the contact phase) are carried out according to the operating conditions given in Example 1.

Table 2B gives the results obtained as regards the electrical characteristics and the biological properties (activation of the contact phase).

TABLE 2B

Electrical characteristics and level of activation of the contact phase for membranes based on Dralon L which are modified or not by addition of PVP

| Membrane | Zeta potential mV | Resistivity ohm.cm | Electro-kinetic index I | Concentration of kallicreins formed, in U/l |
|---|---|---|---|---|
| Dralon L | −39 | 5500 | 0.85 | 24 |
| Dralon L modified by addition of PVP | −14 | 5830 | 0.38 | <10 |

Example 3

A dialyser (trade name Crystal 4000, manufactured by Hospal), consisting of 57 parallel blood compartments separated by a flat AN69 membrane, has a surface area capable of coming into contact with the blood of 1.53 m². This dialyser is made to undergo the following steps:

circulation in the blood compartment of 2 liters of physiological saline at a flow rate of 200 ml/min (ultrafiltration rate of 22 ml/min).

circulation in the blood compartment of 500 ml of a solution PEI with an average molecular mass of greater than 750,000 daltons, at a concentration of 40 mg/l in distilled water and at a flow rate of 200 ml/min (ultrafiltration rate of 22 ml/min).

rinsing by circulation in the blood compartment of 2 liters of a physiological saline solution at a flow rate of 200 ml/min (ultrafiltration rate of 22 ml/min).

retreatment with glycerol by circulation in the blood compartment of 1 liter of a glycerol/water solution (60/40 by mass) at a flow rate of 200 ml/min (ultrafiltration rate of 22 ml/min).

The Zeta potential "Z" is calculated from the measurement of the potential "E" according to the conditions given in the description.

Next, after purging with air, the dialyser is sterilized by gamma irradiation (25 to 36 kGy).

After storage, and after rinsing for 10 minutes by circulation of an NaCl solution (0.15 M) at 200 ml/min, the dialyser is tested as regards its capacity to generate kallicreins on contact with dilute plasma, according to the method described in Example 1 (the flow rate of the biological liquid in the internal compartment of the dialyser is, in this case, 100 ml/min).

TABLE 3

Zeta potential "Z" and level of activation of the contact
phase of the dialysers AN69 and AN69 modified with PEI

| Dialyser | Zeta potential mV | Concentration of kallicreins formed U/l |
|---|---|---|
| Crystal 4000 | −72 | 75 |
| Crystal 4000 treated with PEI | +2.9 | <10 |

Example 4

A flat AN69 membrane (20 μm thickness) is treated by spraying with PEI with an average molecular mass of greater than 750,000 daltons at a concentration of 5 g/kg in a 60/40 by mass glycerol/water mixture. The amount deposited is about 9 mg/m² of membrane.

With this membrane, a dialyser is assembled containing 39 parallel blood compartments separated by the flat AN69 membrane, such that the face treated is the one which is in contact with the blood. The surface area of the membrane intended to come into contact with the blood is about 1.04 m².

The Zeta potential "Z" is calculated from the measurement of the potential "E" according to the conditions given in the description. The flow potential of such a dialyser is equal to +10 μV/mmHg, whereas that of a dialyser of the same type without PEI is equal to −47 μV/mmHg.

Next, after sterilization by gamma irradiation (36 K Gy), the dialyser is tested as regards its capacity to generate kallicreins in contact with dilute plasma, according to the method described in Example 1 (the flow rate of the biological fluid in the internal compartment of the dialyser is, in this case 100 ml/min).

TABLE 4

Zeta potential "Z" and level of activation of the contact
phase of the dialysers AN69 and AN69 modified with PEI

| Dialyser | Zeta potential mV | Concentration of kallicreins formed U/l |
|---|---|---|
| AN69 | −70 | 59 |
| AN69 modified by spraying with PEI | 14.8 | <10 |

Example 5

A dialyser comprising about 8500 hollow AN69 fibers was assembled. The surface area of the membrane intended to come into contact with blood or plasma is about 1.34 m².

200 ml of a solution containing 5 g/kg of PEI (average molecular mass of greater than 750,000 daltons) are prepared in a 60/40 by mass glycerol/water mixture. This solution is made to circulate in the internal compartment of the dialyser in an open circuit at a flow rate of 200 ml/min. The blood compartment, or internal A compartment, is delimited by the interior of the fibers and two caps each fitted with an access tube, which are attached to the ends of the dialyser case. The Zeta potential "Z" is calculated from the measurement of the potential "E" according to the condition en in the description. The flow potential measured with this dialyser is equal to +2.7 μV/mmHg (−22 μV/mmHg in the case of a dialyser of the same type without PEI).

Next, after sterilization by gamma irradiation (36 K Gy), the dialyser is tested as regards its capacity to generate kallicreins on contact with dilute plasma, according to the method described in Example 1.

After rinsing for 10 minutes by circulation of an NaCl solution (0.15 M) at 200 ml/min, the dialyser is subjected to the biological test described in Example 1 (the flow rate of the biological fluid in the internal compartment of the dialyser is, in this case, 100 ml/min).

TABLE 5 below gives the results of the various
measurements carried out and the level of activation of
the contact phase achieved.

| Dialyser | Zeta potential mV | Concentration of kallicreins formed U/l |
|---|---|---|
| AN69 | −72 | 70 |
| AN69 modified with PEI | 9.3 | <10 |

The overall ionic capacity of the hollow fibers in AN69, without PEI, is 174 μeq/g of swollen polymer and the one of the hollow fibers in AN69, modified by PEI, is ※ 163 μeq/g of swollen polymer.

This invention can be used with any type of apparatus which incorporates a semi-permeable membrane for the treatment of blood or plasma.

BRIEF DESCRIPTION OF THE DRAWING

The attached FIGURE is a vertical cross sectional view of a preferred embodiment of apparatus of the invention but is merely intended to be exemplary and limiting of the invention.

DETAILED DESCRIPTION OF AN EXEMPLARY EMBODIMENT DEPICTED IN THE FIGURE

The FIGURE represents a membrane exchanger comprising two compartments which are separated by a semi-permeable membrane composed of a (partially represented) bundle 1 of semi-permeable hollow fibers. The bundle 1 is secured within a tubular housing 2 at both ends by means of two disks 3,4 of potting material. The disks 3,4 tie up the fibers together and they delimit between them within the housing 2 a fluid-tight compartment to which two pipes 5,6 give access, which are perpendicular to the longitudinal axes 9 of the housing 2. Two end caps 7,8 are respectively secured at the ends of the housing 2. Each end cap 7,8 comprises an axial access pipe 9,10. The blood compartment of this exchanger is composed of the lumens of the hollow fibers and of the inner space delimited between the end caps 7,8 and the disks 3,4 of potting material.

Without further elaboration, it is believed that one skilled in the art can, using the preceding description, utilize the present invention to its fullest extent. The preceding preferred specific embodiments are, therefore, to be construed as merely illustrative, and not limitative of the remainder of the disclosure in any way whatsoever.

The entire disclosure of all applications, patents and publications, cited above, and of French application 9716732, filed Dec. 24, 1997, are hereby incorporated by reference.

From the foregoing description, one skilled in the art can easily ascertain the essential characteristics of this invention, and without departing from the spirit and scope thereof, can make various changes and modifications of the invention to adapt it to various usages and conditions.

What is claimed is:

1. A process for manufacturing apparatus for the treatment of blood or plasma by extra-corporal circulation, for preventing activation of the contact phase and comprising a semi-permeable membrane in the form of a flat membrane or a bundle of hollow fibers, based on polyacrylonitrile bearing fixed negative charges, characterized in that it comprises the following steps:

preparing a solution comprising:
   at least one polyacrylonitrile bearing fixed negative charges,
   at least one neutral polymer,
   at least one solvent for said polyacrylonitrile and for the neutral polymer,
optionally, at least one non-solvent for the polyacrylonitrile;
extruding the solution in order to form a hollow fiber or a flat membrane;
simultaneously with extrusion, in the case of the preparation of a hollow fiber, or after extrusion in the case of the formation of a flat membrane, solidifying the membrane obtained by a phase inversion process by partial or total contact of the extruded product with a liquid or gaseous fluid which is chemically inert with respect to the said polymers;
washing the flat membrane or the hollow fiber obtained;
optionally, treating the flat membrane or the hollow fiber with glycerol;
preparing a semi-permeable membrane from the flat membrane or assembling a bundle of hollow fibers from the hollow fiber;
mounting the flat membrane or the bundle of hollow fiber in a case and, optionally fixing caps to the case;
sterilizing the medical apparatus obtained;
and in that the amount of neutral polymer is adjusted such that:
   the overall ionic capacity of the semi-permeable membrane, based on polyacrylonitrile bearing fixed negative charges and containing a neutral polymer, is negative;
   the overall ionic capacity of the semi-permeable membrane, based on polyacrylonitrile bearing fixed negative charges and containing a neutral polymer, is, as an absolute value, not more than 10% less than the overall ionic capacity of the same semi-permeable membrane which contains no neutral polymer;
   the semi-permeable membrane based on polyacrylonitrile bearing fixed negative charges and containing a neutral polymer complies, before sterilization, with the following two electrical characteristics:
   the electrokinetic index "I" of the semi-permeable membrane containing a neutral polymer, which is equal to $Log_{10}(|Z|/R)$, i.e. to the logarithm, in base 10, of the ratio $|Z|/R$ of the Zeta potential "Z", as an absolute value, expressed in microvolts, of the surface of the membrane intended to come into contact with blood or plasma, to the electrical resistivity "R" of the membrane, expressed in ohm.centimetres, is less than or equal to 0.8,
   and the Zeta potential "Z" is negative.

2. A process for manufacturing apparatus for the treatment of blood or plasma by extra-corporal circulation, for preventing activation of the contact phase and comprising a semi-permeable membrane, in the form of a flat membrane or of a bundle of hollow fibers, based on polyacrylonitrile bearing fixed negative charges, characterized in that it comprises the following steps:

(a) preparing a flat membrane or a hollow fiber, which has optionally been treated with glycerol, from a solution of polyacrylonitrile bearing negative charges;
(b) mounting the semi-permeable membrane or a bundle of hollow fibers in a case and attaching caps to said case;
(c) optionally removing the glycerol from the semi-permeable membrane and preparing a solution containing the cationic polymer in dissolved form and bringing said solution into contact with the surface of the semi-permeable membrane intended to be placed in contact with blood, it being possible for step (c) to be carried out before or after step (b),
(d) when the above mentioned step (c) has been carried out subsequent to step (b), purging the apparatus of the solution containing the cationic polymer;
(e) optionally, rinsing the semi-permeable membrane in order to remove excess of non-bound cationic polymer and, optionally, retreating the semi-permeable membrane with glycerol;
(f) sterilizing the medical apparatus;
and in that the amount of cationic polymer is adjusted such that:
   the overall ionic capacity of the semi-permeable membrane, based on polyacrylonitrile bearing fixed negative charges and containing a cationic polymer, is negative;
   the overall ionic capacity of the semi-permeable membrane, based on polyacrylonitrile bearing fixed negative charges and containing a cationic polymer, is, as an absolute value, not more than 10% less than the overall ionic capacity of the same semi-permeable membrane which contains no cationic polymer;
   the semi-permeable membrane based on polyacrylonitrile bearing fixed negative charges and containing a cationic polymer complies, before sterilization, with the following two electrical characteristics:
   the electrokinetic index "I" of the semipermeable membrane containing a cationic polymer, which is equal to $Log_{10}(|Z|/R)$, i.e. to the logarithm, in base 10, of the ratio $|Z|/R$ of the Zeta potential "Z", as an absolute value, expressed in microvolts, of the surface of the membrane intended to come into contact with blood or plasma, to the electrical resistivity "R" of the membrane, expressed in ohm.centimeters, is less than or equal to 0.8,
   and the Zeta potential "Z" is negative.

3. A process for manufacturing apparatus for the treatment of blood or plasma by extra-corporal circulation, for preventing activation of the contact phase and comprising a semi-permeable membrane, in the form of a flat membrane, based on polyacrylonitrile bearing fixed negative charges, characterized in that it comprises the following steps:

(a) preparing a flat membrane, which has optionally been treated with glycerol, from a solution of polyacrylonitrile bearing negative charges;
(b) simultaneously or consecutively, optionally removing the glycerol from the semi-permeable membrane and preparing a solution containing the cationic or neutral polymer in dissolved form and spraying said solution onto the surface of the semi-permeable membrane intended to be placed in contact with blood;

(c) mounting the semi-permeable membrane in a case and attaching caps to said case;

(d) optionally, rinsing the semi-permeable membrane in order to remove the excess of non-bound cationic polymer and, optionally, retreating the semi-permeable membrane with glycerol;

(e) sterilizing the medical apparatus;

and in that the amount of cationic or neutral polymer is adjusted such that:

the overall ionic capacity of the semi-permeable membrane, based on polyacrylonitrile bearing fixed negative charges and containing a cationic or neutral polymer, is negative;

the overall ionic capacity of the semi-permeable membrane, based on polyacrylonitrile bearing fixed negative charges and containing a cationic or neutral polymer, is, as an absolute value, not more than 10% less than the overall ionic capacity of the same semi-permeable membrane which contains no cationic or neutral polymer;

the semi-permeable membrane based on polyacrylonitrile bearing fixed negative charges and containing a cationic or neutral polymer complies, before sterilization, with the following two electrical characteristics:

the electrokinetic index "I" of the semi-permeable membrane containing a cationic or neutral polymer, which is equal to $Log_{10}(|Z|/R)$, i.e. to the logarithm, in base 10, of the ratio $|Z|/R$ of the Zeta potential "Z", as an absolute value, expressed in microvolts, of the surface of the membrane intended to come into contact with blood or plasma, to the electrical resistivity "R" of the membrane, expressed in ohm.centimeters, is less than or equal to 0.8, and the Zeta potential "Z" is negative.

4. An article of manufacture for the treatment of blood or plasma by extra-corporal circulation, which is sterilized and ready to use, for preventing activation of the contact phase and comprising a semi-permeable membrane, in the form of a flat membrane or a bundle of hollow fibers, based on polyacrylonitrile bearing fixed negative charges, characterized in that, before or after formation of the semi-permeable membrane, and before sterilization, at least one neutral or cationic polymer is combined with the semi-permeable membrane, in a sufficient amount such that:

the overall ionic capacity of the semi-permeable membrane, based on polyacrylonitrile bearing fixed negative charges and containing a neutral or cationic polymer, is negative;

the overall ionic capacity of the semi-permeable membrane, based on polyacrylonitrile bearing fixed negative charges and containing a neutral or cationic polymer, is, as an absolute value, not more than 10% less than the overall ionic capacity of the same semi-permeable membrane which contains no neutral or cationic polymer;

the semi-permeable membrane based on polyacrylonitrile bearing fixed negative charges and containing a neutral or cationic polymer complies, before sterilization, with the following two electrical characteristics:

the electrokinetic index "I" of the membrane containing a neutral or cationic polymer is less than or equal to 0.8, "I" being equal to the logarithm, in base 10, of the ratio $|Z|/R$, where "Z" is the Zeta potential as an absolute value, expressed in microvolts, of the surface of the membrane intended to come into contact with blood or plasma, and where "R" is the resistivity of the membrane, expressed in ohm.centimeters, and the Zeta potential is negative.

5. A method for preventing activation of the contact phase of blood or plasma which comes into contact with a semi-permeable membrane based on polyacrylonitrile bearing fixed negative charges, which is fitted in apparatus for the treatment of blood or plasma, by extra-corporal circulation, said method comprising contacting blood or plasma with said semi-permeable membrane, wherein:

a neutral or cationic polymer is combined with said semi-permeable membrane before or after formation of the membrane, and before sterilization of the membrane;

the overall ionic capacity of the semi-permeable membrane, based on polyacrylonitrile bearing fixed negative charges and containing a neutral or cationic polymer, is negative;

the overall ionic capacity of the semi-permeable membrane, based on polyacrylonitrile bearing fixed negative charges and containing a neutral or cationic polymer, is, as an absolute value, not more than 10% less than the overall ionic capacity of the same semi-permeable membrane without a neutral or cationic polymer, at least some of at least one of said neutral or cationic polymers being present at the surface of the membrane;

the semi-permeable membrane based on polyacrylonitrile bearing fixed negative charges and containing a neutral or cationic polymer complies, before sterilization, with the following two electrical characteristics;

the electrokinetic index "I" is less than or equal to 0.8, "I" being equal to the logarithm, in base 10, of the ratio $|Z|/R$, where "Z" is the Zeta potential, as an absolute value, expressed in microvolts, of the surface of the membrane intended to come into contact with blood or plasma, and where "R" is the electrical resistivity of the membrane, expressed in ohm.centimeters, and the Zeta potential "Z" is negative.

6. A method according to claim 5, characterized in that the electrokinetic index "I" of the semi-permeable membrane based on polyacrylonitrile bearing fixed negative charges and containing a neutral or cationic polymer is not more than 0.7.

7. A method according to claim 6, characterized in that the electrokinetic index "I" of the semi-permeable membrane based on polyacrylonitrile bearing fixed negative charges and containing a neutral or cationic polymer is not more than 0.6.

8. A method according to claim 5, characterized in that the overall ionic capacity of the semi-permeable membrane based on polyacrylonitrile bearing fixed negative charges and containing a neutral or cationic polymer is less than −30 $\mu$eq/g of swollen polymer.

9. A method according to claim 8, characterized in that the overall ionic capacity of the semi-permeable membrane based on polyacrylonitrile bearing fixed negative charges and containing a neutral or cationic polymer is less than −50 $\mu$eq/g of swollen polymer.

10. A method according to claim 5, characterized in that the overall ionic capacity of the semi-permeable membrane based on polyacrylonitrile bearing fixed negative charges and containing a neutral or cationic polymer is, as an absolute value, not more than 1% less than the overall ionic capacity of the same semi-permeable membrane which does not contain a neutral or cationic polymer.

11. A method according to claim 5, characterized in that the polymer is neutral and has an average molecular mass of greater than 40,000 daltons.

12. A method according to claim 11, characterized in that the neutral polymer has an average molecular mass of greater than 100,000 daltons.

13. A method according to claim 11, characterized in that the neutral polymer is chosen from the group consisting of polyvinylpyrrolidones and polyethylene glycols.

14. A method according to claim 5, characterized in that the polymer is cationic and has an average molecular mass of greater than 25,000 daltons.

15. A method according to claim 14, characterized in that the cationic polymer has an average molecular mass of greater than 100,000 daltons.

16. A method according to claim 14, characterized in that the cationic polymer is chosen from polyamines, optionally polyethyleneimines.

17. A method according to claim 16, wherein the cationic polymer is a polyethylene amine.

18. A method according to claim 14, characterized in that the cationic polymer is chosen from dimethylaminoethyl dextrans.

19. A method according to claim 5, characterized in that the polyacrylonitrile constituting the semi-permeable membrane is a copolymer of acrylonitrile and of at least one anionic or anionizable monomer containing where appropriate, units derived from olefinic unsaturation which is capable of being copolymerized with acrylonitrile.

20. A method according to claim 19, characterized in that the polyacrylonitrile is a copolymer of acrylonitrile and of an olefinically unsaturated anionic or anionizable comonomer bearing sulphonate, carboxyl, phosphate, phosphonate and sulphate groups.

21. A method according to claim 20, characterized in that the comonomer is sodium methallyl sulphonate.

22. A method according to claim 5, characterized in that the polyacrylonitrile constituting the semi-permeable membrane is a copolymer of acrylonitrile and of at least one nonionic and non-ionizable monomer containing olefinic unsaturation which is capable of being copolymerized with acrylonitrile.

* * * * *